United States Patent [19]
Carter

[11] 3,966,944
[45] June 29, 1976

[54] 10 (N-METHYL-4-PIPERIDYLIDENE)-10H[1]-BENZOPYRANO[3,2-b]-PYRIDINE AS AN ANALGESIC, ANTI-INFLAMMATORY AND AGENT AGAINST TYPE III HYPERSENSITIVITY DISEASE

[75] Inventor: George W. Carter, Libertyville, Ill.

[73] Assignee: Abbott Laboratories, North Chicago, Ill.

[22] Filed: May 19, 1975

[21] Appl. No.: 578,583

[52] U.S. Cl. .............................................. 424/263
[51] Int. Cl.² ........................................ A61K 31/44
[58] Field of Search ........................... 424/267, 263

[56] References Cited
UNITED STATES PATENTS 3,803,153  4/1974  Villani ......................... 260/293.53

*Primary Examiner*—Stanley J. Friedman
*Attorney, Agent, or Firm*—Robert L. Niblack

[57] ABSTRACT

A method of treating analgesia, inflammation and Type III hypersensitivity disease comprising administering a therapeutically effective dose of 10 (N-methyl-4-piperidylidene)-10H[1]-benzopyrano[3,2-b]-pyridine.

2 Claims, No Drawings

10 (N-METHYL-4-PIPERIDYLIDENE)-10H[1]-BENZOPYRANO[3,2-B]-PYRIDINE AS AN ANALGESIC, ANTI-INFLAMMATORY AND AGENT AGAINST TYPE III HYPERSENSITIVITY DISEASE

DETAILED DESCRIPTION OF THE INVENTION

This invention relates to a method of treating analgesia, inflammation and Type III hypersensitivity disease using 10 (N-methyl-4-piperidylidene)-10H[1]-benzopyrano[3,2-b]-pyridine.

Compound 10 (N-methyl-4-piperidylidene)-10H[1]-benzopyrano[3,2-b]-pyridine has been previously reported to be useful as a bronchiodilator, as a CNS agent, and to act within the body to prevent the release of histamine (British Pat. No. 1,373,246). It has now been found that the compound 10 (N-methyl-4-piperidylidene)-10H[1]-benzopyrano[3,2-b]-pyridine possesses analgetic and anti-inflammatory effects and acts against Type III hypersensitivity disease.

Compound 10 (N-methyl-4-piperidylidene)-10H[1]-benzopyrano[3,2-b]-pyridine is represented by

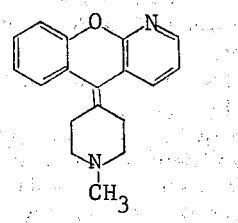

10 (N-methyl-4-piperidylidene)-10H[1]-benzopyrano[3,2b]-pyridine can be prepared according to the method taught in British Pat. No. 1,373,246.

Although, the etiology of Rheumatoid arthritis remains obscure, it is almost certain that immunological mechanisms play an important role in the pathogenesis of this disease. Therefore, inflammation induced by immunological reactions, which are believed to be important in the inflammatory processes of rheumatoid arthritis, make particularly desirable tools for the screening of potential anti-inflammatory agents. Obviously, the usefulness of such a model depends upon how closely it represents the underlying pathological mechanisms of rheumatoid arthritis.

Based upon currently available evidence, a plausible sequence of events leading to the joint leisions in rheumatoid arthritis can be constructed. An initiating antigen, perhaps a transient synovial infection, results in an immune response and retention of the antigen within the joint structure. The interaction of antigen with developing antibodies results in the deposition of immune complexes. These complexes may fix and activiate complement, causing the generation of a number of phlogistic and chemotactic substances. Phagocytosis of the complexes by attracted polymorphonuclear leukocytes (PMNs) leads to the release of lysosomal constituents. The enzymes released from lysosomes can erode articular cartilage and produce inflammation in the joint. The striking resemblance of these events to the Arthus phenomenon point to the potential utility of the Arthus reaction as a screen for anti-inflammatory compounds.

The Arthus reaction represents one of the oldest and best studied models of immunological injury. It is produced by the injection of antigen locally into a hyperimmunized animal or by the injection of a small amount of antibody into the skin of an animal that has just previously been given a large amount of soluble antigen intravenously. In both cases the antigen and antibody become deposited in the walls of small venules. Plasma complement is rapidly bound and activated. Within a few hours neutrophils (PMNs) accumulate, resulting in disruption of the basement membrane of vessel walls and marked edema and hemorrage in the surrounding tissue.

The reverse Arthus reaction offers several advantages over the existing primary screen, carrageenin induced rat paw edema.

1. Unlike carrageenin induced edema, the Arthus reaction is a well characterized immune reaction, which bears close resemblance to the pathogenesis of rheumatoid arthritis.

2. With the exception of steroids, agents that are effective in inhibiting carrageenin edema (tested so far) are not very active against the Arthus reaction.

3. Compounds that produce good inhibition of the Arthus reaction, theoretically, should have the ability in the clinical treatment of rheumatoid arthritis to retard the progression of the disease.

4. Compounds that are "active" in the Arthus reaction may have therapeutic utility in the treatment of other immune complex disorders, such as systemic lupus erythematosus, post-streptococcal nephritis, malarial nephritis, penicillin hypersensitivity, farmer's lung, insect bites, rubella arthritis and gonococcal arthritis.

Antibody Excess (Arthus Type Reactivity)

Maurice Arthus found that injection of soluble antigen intradermally into hyperimmunized rabbits with high levels of precipitating antibody produced an erythematous and oedematous reaction reaching a peak at 3–8 hours and then usually resolving. The lesion was characterized by an intense infiltration with polymorphonuclear leukocytes injected antigen precipitates with antibody often within the venule and the complex binds complement; using the appropriate fluorescent reagents, antigen, immunoglobulin and complement components can all be demonstrated in this lesion. Anaphylatoxin is soon generated and causes histamine liberation. Local intravascular complexes will cause platelet aggregation and vasoactive amine release. This early phase is seen readily in man as an erythematous reaction which should not be confused with the immediate anaphylactic Type I skin response. The formation of chemotactic factors leads to the influx of polymorphs and, as a result, erythema and oedema increase. The Arthus reaction can be blocked by depletion of complement or of the neutrophil polymorphs (by nitrogen mustard or specific anti-polymorph sera).

Intrapulmonary Arthus-type reactions to inhaled antigen appear to be responsible for a number of hypersensitivity disorders in man. The severe respiratory difficulties associated with farmer's lung occur with 6–8 hours of exposure to the dust from mouldy hay. The patients are found to be sensitized to thermophilic actinomycetes which grow in the mouldy hay and extracts of these organisms give precipitin reactions with the subject's serum and Arthus reactions on intradermal injection. Inhalation of bacterial spores present in dust from the hay introduces antigen into the lungs and a complex-mediated hypersensitivity reaction occurs.

A similar situation arises in pigeon-fancier's disease where the antigen is probably serum protein present in the dust from dried faeces, and in many other cases where potentially antigenic materials are continually inhaled.

When an individual has been immunologically primed or sensitized, further contact with antigen can lead not only to secondary boosting of the immune response but can also cause tissue-damaging reactions. We speak of hypersensitivity reactions and a state of hypersensitivity. Coombs and Gell defined four types of hypersensitivity, to which can be added a fifth, viz. 'stimulatory', which they mention. Types I, II, III and V depend on the interaction of antigen with humoral antibody and tend to be called 'immediate' type reactions although some are more immediate than others! Type IV involves receptors bound to the lymphocyte surface and because of the longer time course this has in the past been referred to as 'delayed-type sensitivity'.

Type I — Anaphylactic-Type Sensitivity

The antigen reacts with a specific class of antibody bound to mast cells or circulating basophils through a specialized region of the Fc piece. This leads to degranulation of the mast cells and release of vasoactive amines. These antibodies are termed homocytotropic (also referred to as reagins).

Type II — Cytotoxic-Type Hypersensitivity

Antibodies binding to an antigen on the cell surface cause (i) phagocytosis of the cell through opsonic (Fc) or immune (C3) adherence, (ii) non-phagocytic extracellular cytotoxicity by killer (K) cells with receptors for IgFc and (iii) lysis through the operation of the full complement system up to C8, 9.

Type III — Complex-Mediated Hypersensitivity

The formation of complexes between antigen and humoral antibody can lead to activation of the complement system and to the aggregation of platelets with the following consequences:
1. Microthrombi,
2. Vasoactive Amine Release,
3. Proteolytic Enzyme Release, and
4. Histamine Release Type IV — Cell-Mediated (Delayed-Type) Hypersensitivity Thymic derived T-lymphocytes bearing specific receptors on their surface are stimulated by contact with antigen to release factors (termed 'lymphokines' by Dumonde) which mediate delayed-type hypersensitivity (e.g. Mantoux test for tuberculin sensitivity); in the reaction against tissue transplants, the stimulated lymphocytes transform into blast-like cells capable of killing target cells bearing the histocompatibility antigens of the graft.

Type V — Stimulatory Hypersensitivity

Non-complement fixing antibodies directed against certain cell surface components may actually stimulate rather than destroy the cell. Theoretically, stimulation could also occur through the development of antibodies to naturally occurring mitotic inhibitors in the circulation.

Generally speaking, 10 N-methyl-4-piperidylidene)-10H[1]-benzopyrano[3,2-b]-pyridine is useful as an analgesic or anti-inflammatory when administered to human patients in need of such treatment in dosages of 0.01 to 25 mg per day, and generally 0.5 to 15 mg per day. The exact dosage, of course, should be prescribed by a physician. In lower warm blooded mammals, the dosage should be 0.75 to 25 mg/kg of body weight.

The following examples further illustrate the invention:

EXAMPLE I

Reverse Passive Arthus Reaction

Materials:
Bovine Serum Alumin 15 mg./20 ml. = 0.075%
Dissolve B.S.A. in several ml. 0.9% saline, add 4 ml. of 1.0% solution of Evans Blue Dye, q.s. to 20 ml. with saline to give a final concentration of B.S.A. equal to 0.075%, and Evans Blue 0.2%.
(Anti-B.S.A.) 43.2 mg./ 3 ml. (Ammonium Sulfate precipitated rabbit serum containing anti-BSA)
To 43.2 mg. Anti-B.S.A. add 0.75 ml. Di_tilled $H_2O$ and 2.25 ml. 0.9% saline to give an isotonic solution.

Methods:
Male Sprague-Dawley rats weighing approximately 130–160 g. are used, 4 rats per group. All animals are injected intravenously with 0.5 ml. B.S.A. + Evans Blue solution.
Each rat then receives an oral dose of drug; one drug is administered per group.
Thirty minutes subsequent to drug dosing, each animal is injected intradermally with 0.05 ml. Anti-B.S.A. into the dorsal skin. 4 hours later the animals are sacrificed, the dorsal skin reflexed, and the lesion excised. 2 perpendicular diameters of each lesion are measured. The average diameters of the lesions from the treated groups are compared with the average diameters from the control group to determine any drug effect.

The effect of 10 (N-methyl-4-piperidylidene)-10H[1]-benzopyrano[3,2-b]-pyridine on the reverse passive Arthus reaction.

| Dose of Compound mg/kg. PO | % Inhibition of the Inflammatory Lesion Area |
| --- | --- |
| 10 | 82.9 |
| 5 | 81.2 |
| 2.5 | 70.9 |
| 1.5 | 64.4 |
| 0.75 | 43.2 |

Calculated $ED_{50}$ value is 0.78 mg/kg (.07, 1.5)

The effects of 10 (N-methyl-4-piperidylidene)-10-H[1]-benzopyrano[3,2-b]-pyridine in the Arthus reaction are not due to its anti-histamine or antiserotamin activity because chlorpheninamine at 10 mg/kg, P.O. and cyproheptadine at 5 mg/kg P.O. were completely inactive in the reverse passive Arthus reaction.

EXAMPLE II

Analgesic Activity of 10 (N-Methyl-4-Piperidylidene)-10H[1]-Benzopyrano[3,2-b]-Pyridine — Mouse Writhing Method Modified method of Whittle (Brit. J. Pharmacol. 1964, 22:246) — Groups of 5 mice administered various dose-levels of the compound 30 minutes prior to the IP injection of 0.5% acetic acid (0.4 ml). Writhing counted for a 20 minute period following the acid injection.

| Oral Treatment | | Ave. No. of Writhes/Mouse (±S.D.) | % Inhibition |
|---|---|---|---|
| Control Saline | 20 ml/kg | 34.8 (8.8) | — |
| A-45637 | 10 mg/kg | 31.4 (16.7) | 9.8 |
| A-45637 | 20 mg/kg | 18.0 (8.3) | 48.3 |
| A-45637 | 40 mg/kg | 15.8 (8.0) | 54.6 |
| A-45637 | 80 mg/kg | 6.6 (4.6) | 81.0 |

$ED_{50}$ = 29.7 mg/kg P.O.
95% CL (10.9–98.0)

EXAMPLE III

Carrageenin Induced Rat Paw Edema

The carrageenin induced rat paw edema test of Winter, et al. (Proc. Soc. Exp. Biol. and Med., 1962, 111:544) and modified by Van Arman, et al. (J. Pharmacol. Exp. Therap., 1965, 150:328) is used as a primary test for anti-inflammatory activity.

Groups of male Sprague-Dawley rats weighing 160–220 grams are used to compare various dose levels of the test compound to control animals. The compound is administered orally to the respective groups 1 hour prior to a sub-plantar injection into the left hind paw with 0.1 ml of a 1.5% suspension of carrageenin in saline. The paws are measured volumetrically by mercury displacement prior to (normal paw), 1.5, 3 and 5 hours after the carrageenin injection.

Activity is calculated as the percent difference (inhibition) between the increases in paw size (edema) of the test groups compared to the control groups.

| DOSE | % INCREASE IN PAW SIZE OVER NORMAL | % INHIBITION OF EDEMA (3 HR. READING) |
|---|---|---|
| 0.5% MC Control | 89.3% | — |
| 16 mg/kg | 33.1% | 62.9% |
| 8 mg/kg | 50.0% | 44.0% |
| 4 mg/kg | 55.3% | 38.1% |
| 2 mg/kg | 66.9% | 25.1 |

$ED_{50}$ = 8.73 (5.43, 23.72)
$ED_{25}$ = 2.04 (0.34, 3.55)

The present invention includes within its scope pharmaceutical compositions comprising 10 (N-methyl-4-piperidylidene)-10H[1]-benzopyrano[3,2-b]-pyridine in association with a pharmaceutically acceptable carrier or diluent. 10 (N-methyl-4-piperidylidene)-10H[1]-benzopyrano[3,2-b]-pyridine exhibits both oral and parenteral activity and can be formulated in dosage forms for oral, sublingual, parenteral or rectal administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents.

Liquid dosage forms for oral administration include pharmaceutically acceptable emulsions, solutions, suspensions, syrups and elixirs containing inert diluents commonly used in the art, such as water. Beside inert diluents, such compositions can also include adjuvants, such as wetting agents, emulsifying and suspending agents, and sweetening, flavoring and perfuming agents.

Preparations according to this invention for parenteral administration include sterile aqueous or non-aqueous solutions, suspension or emulsions. Examples of non-aqueous vehicles are propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water or some other sterile injectable medium immediately before use.

Compositions for rectal administration are suppositories which may contain, in addition to the active substance, excipients such as cocoa butter or a suppository wax.

The dosage of active ingredient in the compositions of this invention may be varied; however, it is necessary that the amount of the active ingredient be such that a suitable dosage form is obtained.

It will be understood that the compound useful in the practice of this invention can be administered as the free base or as a pharmaceutically acceptable acid addition salt. The term "pharmaceutically acceptable acid addition salt", as used herein refers to a non-toxic salt prepared by reacting the free base with a suitable organic or inorganic acid. Representative salts include the hydrochloride, hydrobromide, sulfate, bisulfate, acetate, valerate, oleate, laurate, borate, benzoate, lactate, phosphate, tosylate, citrate, maleate, fumerate, succinate, tartrate, and the like.

We claim:

1. The method of treating analgesia inflammation and Type III hypersensitivity disease in a mammalian patient in need of such treatment comprising administering to said patient a therapeutically effective amount of 10 (N-methyl-4-piperidylidene)-10H[1]-benzopyrano[3,2-b]-pyridine.

2. The method of claim 1 wherein from 0.01 to 25 mg/kg of body weight daily of 10 (N-methyl-4-piperidylidene)-10H[1]-benzopyrano[3,2-b]-pyridine is administered to said patient.

* * * * *